US009370177B2

(12) United States Patent
Bajomi et al.

(10) Patent No.: US 9,370,177 B2
(45) Date of Patent: Jun. 21, 2016

(54) CONSUMABLE AQUEOUS GEL FOR USE IN PEST CONTROL, A PEST CONTROL DEVICE COMPRISING AN AQUEOUS GEL, AND THE USE OF AN AQUEOUS GEL IN A PEST CONTROL DEVICE AND IN A METHOD OF CONTROLLING PESTS

(75) Inventors: Daniel Bajomi, Budapest (HU); Janos Daru, Budapest (HU); Lajos Fekete, Torokbalint (HU); Attila Halasi, Budapest (HU); Vince Pozsar, Acs (HU); Jozsef Schmidt, Bicske (HU); Janos Szilagyi, Budapest (HU); Laszlo Takacs, Budapest (HU); Jozsef Tomcsik, Budapest (HU)

(73) Assignee: Babolna Bio Ltd., Budapest (HU)

( * ) Notice: Subject to any disclaimer, the term of this patent is extended or adjusted under 35 U.S.C. 154(b) by 53 days.

(21) Appl. No.: 14/367,037

(22) PCT Filed: Dec. 22, 2011

(86) PCT No.: PCT/IB2011/003263
§ 371 (c)(1),
(2), (4) Date: Nov. 5, 2014

(87) PCT Pub. No.: WO2013/093543
PCT Pub. Date: Jun. 27, 2013

(65) Prior Publication Data
US 2015/0147289 A1 May 28, 2015

(51) Int. Cl.
*A01N 25/02* (2006.01)
*A01M 25/00* (2006.01)
*A01M 29/34* (2011.01)
*A01N 25/04* (2006.01)
*A01N 25/34* (2006.01)
*A01N 37/44* (2006.01)
*A01N 41/04* (2006.01)
*A01N 43/80* (2006.01)
*A01N 59/08* (2006.01)

(52) U.S. Cl.
CPC .............. *A01N 25/04* (2013.01); *A01M 25/002* (2013.01); *A01N 25/34* (2013.01); *A01N 37/44* (2013.01); *A01N 41/04* (2013.01); *A01N 43/80* (2013.01); *A01N 59/08* (2013.01)

(58) Field of Classification Search
CPC ............................ A01N 25/04; A01M 25/002
See application file for complete search history.

(56) References Cited

U.S. PATENT DOCUMENTS

| 5,238,681 | A | 8/1993 | Chang et al. |
| 5,300,302 | A | 4/1994 | Tachon et al. |
| 5,501,033 | A * | 3/1996 | Wefler ................ A01M 1/2016 43/131 |
| 6,792,713 | B2 * | 9/2004 | Snell ................... A01M 1/2005 43/124 |
| 2004/0180071 | A1 | 9/2004 | Marshall |
| 2005/0181003 | A1 | 8/2005 | Endepols et al. |

FOREIGN PATENT DOCUMENTS

| EP | 0288420 | 10/1988 |
| GB | 2467199 | 7/2010 |
| WO | 2008031870 | 3/2008 |

OTHER PUBLICATIONS

European Patent Office, PCT International Preliminary Report on Patentability, Jul. 25, 2014.
International Search Report (6 pgs.) and Written Opinion of the International Searching Authority (14 pgs.), European Patent Office, Nov. 26, 2012.
Abstract of Appel and M J Tanley A G "Laboratory and Field Performance of an Imidacloprid Gel Bait Against German Cockroaches (Dictyoptera: Blattellidae)", Journal of Economic Entomology, Entomological Society of America, Landham, MD, US, vol. 93, No. Feb. 1, 2000, pp. 112-118, XP007920496, ISSN: 0022-0493.
Abstract of Godfrey Nalyanya et al: "Attractiveness of Insecticide Baits for Cockroach Control (Dictyoptera: Blattelidae) Laboratory and Field Studies", Journal of Economic Entomology, Entomological Society of America, Landham, MD, US, vol. 94, No. 3, Jan. 1, 2001, pp. 686-693, XP007920497, ISSN: 0022-0493.
Abstract of Jules Silverman and T Ai H Roulston: :"Acceptance and Intake of Gel and Liquid Sucrose Compositions by the Argentine Ant (Hymenoptera: Formicidae)", Journal of Economic Entomology, Entomological Society of America, Landham, MD, US, vol. 94, No. 2, Jan. 1, 2001, pp. 511-515, XP007920495, ISSN: 0022-0493.

* cited by examiner

*Primary Examiner* — Gina Justice
(74) *Attorney, Agent, or Firm* — Wood Herron & Evans LLP

(57) ABSTRACT

A consumable aqueous gel is provided for use in pest control. The gel sates the thirst of pests and increases the consumption of bait by pests. The gel is substantially free of biocides. The gel may be provided as a combination for use in a pest control device. The combination comprises an aqueous gel which is substantially free of biocides and a bait. A pest control device comprises a container having a first compartment containing an aqueous gel which is substantially free of biocides. A method of controlling pests comprises the step of deploying any of the aforementioned aqueous gel, combination according or pest control device. An aqueous gel which is substantially free of biocides may be used with or in a pest control device.

15 Claims, 2 Drawing Sheets

Figure 1:
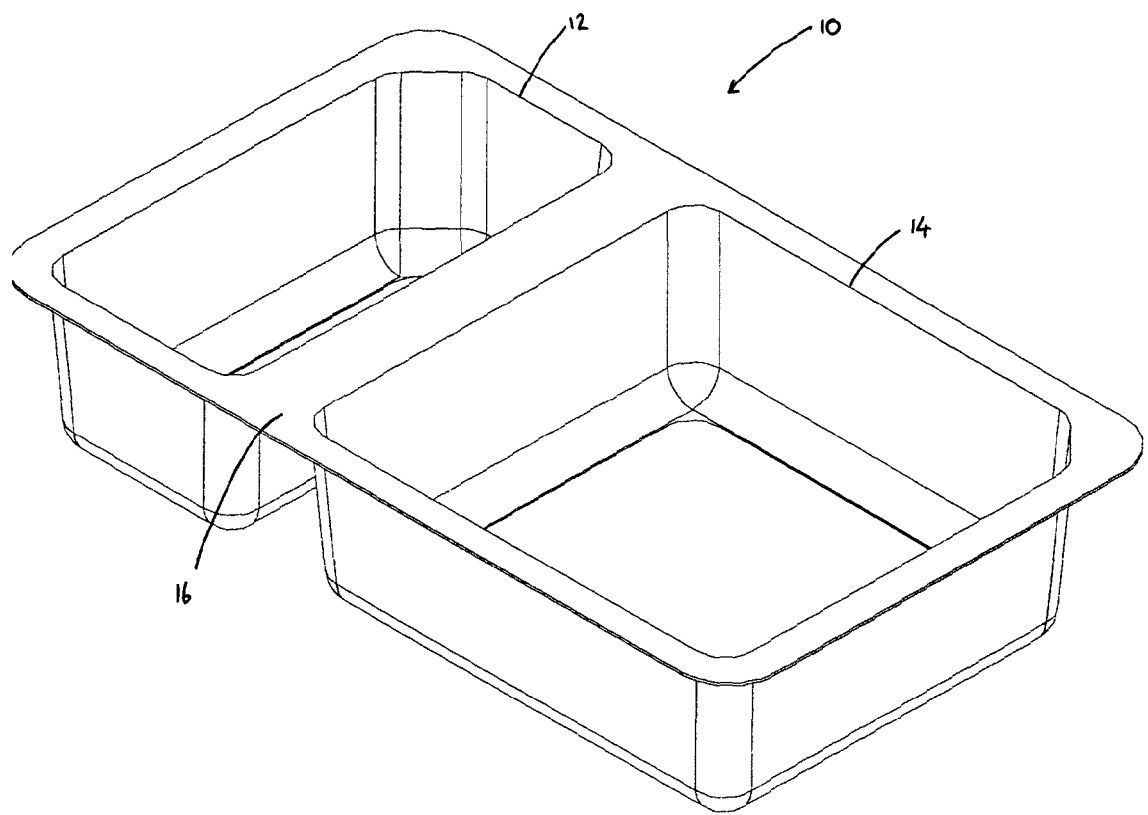

CONSUMABLE AQUEOUS GEL FOR USE IN PEST CONTROL, A PEST CONTROL DEVICE COMPRISING AN AQUEOUS GEL, AND THE USE OF AN AQUEOUS GEL IN A PEST CONTROL DEVICE AND IN A METHOD OF CONTROLLING PESTS

This application claims priority, under Section 371 and/or as a continuation under Section 120, to PCT Application No. PCT/IB2011/003263, filed on Dec. 22, 2011.

The invention relates to a consumable aqueous gel for use in pest control, to a pest control device comprising an aqueous gel and to the use of the gel in a pest control device and in a method of controlling pests. More particularly, the invention relates to the aforementioned aspects wherein the aqueous gel is substantially free of biocides.

Rodents, insects and other pests are a nuisance. They often carry and spread disease; they can cause great damage to products, particularly foodstuffs; and their presence can be distressing, or at least irritating to humans, pets and livestock. Accordingly, control of rodents, insects and other pests (henceforth generally referred to as "pest control") is of great importance.

Of course, various pest control techniques are known in the art. A common pest control technique involves laying devices such as mechanical or electrical traps, or adhesives, to entrap or destroy a pest. An example with which those skilled in the art will be familiar is the sprung rodent trap, first disclosed in U.S. Pat. No. 528,671. With this device, a spring-loaded hammer befalls any trespassing rodent which steps upon a trigger, to which the rodent is preferably drawn by an appealing piece of cheese (or other bait). Since the disclosure of that basic mechanical trap, more sophisticated devices have been devised, and are now known to include features such as alarms or means for giving a pest an electric shock. One such mechanical device is disclosed in the international patent application number WO 99/018780 A1. This document describes a highly efficient rodent trap, which contains bait in order to lure the rodent into the trap, and which kills the rodent by electric shock.

An altogether different class of pest control technique involves the use of chemicals, which are used to poison pests which consume them. Such poisons may include (but are not limited to) pesticides and/or rodenticides. Because chemical pest-control techniques exploit a pest's natural predilection for eating without also requiring a mechanical contraption of which a pest may learn to be suspicious, they have become very successful. Moreover, since chemical pest controls may be provided in a variety of forms, they may be deployed in a much wider variety of situations than mechanical devices. For instance, international patent application numbers WO 95/24124 and WO 01/20983 disclose water-based matrices such as pastes which include toxic baits. These pastes can be applied to cracks, and the like, for poisoning cockroaches and other insects. However, chemical pest-control devices face several problems which are not encountered by their mechanical counterparts.

A significant problem of chemical pest-control devices is that it is necessary, yet can be difficult, to prevent other creatures or humans (particularly children) from accessing the poisonous composition. Unlike mechanical devices, which are usually targeted to a particular pest by design, pesticides, rodenticides and other chemicals may be very damaging to other animals. One way of addressing this problem is to provide the composition comprising the poison in a bait station or delivery apparatus which restricts access to only those pests capable of entering the apparatus. Examples of such stations are given in the following documents.

A plastic bait station is taught in U.S. Pat. No. 4,031,653. The station comprises a series of modules each having an entrance and exit sized to allow a rodent to pass through, but preventing access by children and other animals. A poisonous substance may be provided within the modules, along with food and water. A similar modular bait station for rodents is disclosed in U.S. Pat. No. 3,965,609 and an equivalent station for insects is disclosed in US application number US 2005/0000147.

Another problem with chemical pest controls manifests itself when the compositions are used in an external environment. Often, rain water or moisture in the air may dissolve components of solid compositions, which are therefore not durable in that environment. In contrast, liquid compositions may evaporate. To solve this problem, US patent application number US 2004/0180071 A1 discloses a gel comprising a pesticide along with other ingredients, the gel being substantially weatherproof and resistant to dehydration. Likewise, US patent application number US 2005/0181003 A1 discloses an improved water-based rodenticide gel which is longer lasting than other known pastes and flowable baits. The gel taught in this document does not cure, retains is viscosity and adheres permanently to surfaces, negating the need for bait boxes. U.S. Pat. No. 7,276,232 B2 also describes rodenticides which are to be used in gelatinized form, where the gelatinizing materials may be cellulose derivatives, xantans, PVAs, polyacrylic acids, polyvinyl-pyrrolidones, and inorganic gels. According to this document, the gelatinized form prolongs the efficacy of the active ingredient.

Perhaps the greatest problem facing chemical pest control devices is that some pests, particularly rodents, may develop an aversion to consuming poison and learn to avoid it. In this respect, chemical pest-control techniques suffer the same drawback as the mechanical devices mentioned above. This drawback has been addressed, and overcome to a limited extent, by stations which provide a source of water adjacent the poison. The water attracts the pest to the locality of the poison. Once lured, the chances of the pest encountering the poison are increased. A particularly effective trap is disclosed in WO 2009/121968, which teaches a device having a water reservoir accessible only through an entrance passage lined with a contact pesticide. Insects attracted by the water reservoir crawl over the contact pesticide and thus meet their demise.

A development of this idea may be found in U.S. Pat. No. 5,501,033 and WO 00/76312 which disclose stations for controlling insects. The stations comprise means for sequentially supplying two liquids to an absorbent feeding pad, the first liquid being attractive to the insect to lure it to the station and the second comprising a toxic substance which kills the insect. These stations are successful because the insect becomes trained to feed from the feeding pad which is initially saturated with the benign liquid and, once trained, is subsequently poisoned following the introduction of the toxic substance.

Other packages which operate by luring the pest with an attractant to increase the likelihood of the pest consuming the accompanying poisonous composition are disclosed in GB 2190839, U.S. Pat. No. 4,746,033, US 2005/0000147, and U.S. Pat. No. 4,251,946. In each case, the attractant is water or a water-soluble solid material.

A significant disadvantage of the aforementioned packages is that the pest may simply state its desire for the attractant without consuming the poisonous substance. This problem has been traversed in the prior art in one of two ways.

Firstly, pest control stations are known which provide compartments offering a liquid bait and a solid bait, both of which are poisonous. Examples of such stations, for rodents and insects respectively, are disclosed in US 2010/0319239, U.S. Pat. No. 5,038,516, U.S. Pat. No. 5,857,268, U.S. Pat. No. 6,671,999, U.S. Pat. No. 1,964,611 and US 2005/0252074, for example. In these stations, the pest will be poisoned regardless of whether it is attracted by the food or drink. However, these stations suffer the same disadvantage mentioned above, in that the pest may become develop an aversion to the poisonous material and learn to avoid such stations altogether.

A preferred solution is therefore to render the poison difficult for the pest to detect by mixing the poison in compositions which rodents and other pests would like to consume. For example, pest control compositions may comprise pesticides and/or rodenticides mixed with bait consisting of a substance known to be appealing to the pest. Such substances are known, for example, from Hungarian Patent No. HU 0402059 which describes an appetizer substance, which is mixed with a foodstuff, consisting of trisodium pyrophosphate combined with flavouring and a taste enhancer.

Rodenticides are often mixed into compositions which rodents are apt to consume, such as crop and/or fruit aggregates, grists, flours and mixtures containing animal parts (particularly parts of insects). For example, Belgian patent publication number BE 904203 describes a rodenticide based on vegetables and fruits comprising a hollow crust, inside of which a bait is also provided; European patent application EP 1279334 A1 describes a combined pesticide used against rats; and European patent EP 1279334 B1 discloses a mixture of a paste which is appealing to rodents and a solid chewable component which is adapted to encourage rodents to chew.

US 2005/0181003 A1, US 2004/0180071 A1, WO 2008/031870 A2 and papers A. G. Appel and M, J. Tanley: "Laboratory and Field Performance of an Imidacloprid Gel Bait Against German Cockroaches (Dictyoptera: Blattellidae)", Journal of Economic Entomology, Vol. 93, No. 1, pp. 112-118 (2000) and G. Nalyanya et al.: "Attractiveness of Insecticide Baits for Cockroach Control (Dictyoptera: Blattellidae)", Journal of Economic Entomology, Vol. 94, No. 3, pp. 686-693 (2001) disclose compositions which comprise aqueous gels and a bait and/or a biocide mixed together. The paper J. Silverman and T'ai H. Roulston: Acceptance and Intake of Gel and Liquid Sucrose Compositions by the Argentine Ant (Hymenoptera: Formicidae), Journal of Economic Entomology, Vol. 94, No. 2, pp. 511-515 (2001) discloses a gel which is adapted for intaking a bait. GB 2467199 A, U.S. Pat. No. 5,300,302 A and EP 0288420 A1 disclose aqueous gels. U.S. Pat. No. 5,238,681 A disclose an insect bait station comprising insecticide in a compartment and gel pieces in another compartment, which compartments are separated by a semipermeable membrane.

A problem which the inventors have identified with the aforementioned compositions is that because the poisoned material is less densely distributed (due to the inclusion of an attractant in the mixture) rodents often stop consuming them before they have eaten sufficient rodenticide for it to be effective. This is not desirable as it significantly limits the mortality rate of rodents which can be achieved using this type of pest control device.

Accordingly, the present invention seeks to provide a means of encouraging rodents, and other pests, to consume a larger volume of poisonous material to increase the effectiveness of compositions such as those described above. The inventors have found that rodents interrupt their consumption of the composition because they are thirsty, and choose to leave the composition to seek out a drink. However, providing a source of water adjacent the poisonous composition is unsatisfactory for the reasons given above.

In view of the foregoing, the present invention provides, in a first aspect, a consumable aqueous gel for use in pest control, wherein the gel sates the thirst of pests and increases the consumption of bait by pests, and wherein the aqueous gel is substantially free of biocides.

Also provided, in a second aspect, is a combination (or kit) for use in a pest control device, comprising an aqueous gel; and a bait, wherein the aqueous gel is substantially free of biocides.

Also provided, in a third aspect, is a pest control device comprising a container having a first compartment containing an aqueous gel, wherein the aqueous gel is substantially free of biocides.

Also provided, in a fourth aspect, is a method of controlling pests comprising the step of deploying an aqueous gel according to the aforementioned first aspect, a combination according to the aforementioned second aspect, or a pest control device according to the aforementioned third aspect.

Also provided, in a fifth aspect, is a use of an aqueous gel with or in a pest control device, wherein the aqueous gel is substantially free of biocides.

Preferred features of the gel, combination, device, method and use are specified in the dependent claims.

By "substantially free of biocides", this description means that the gel does not cause an adverse reaction in a pest, in particular in a rodent or insect. In other words, "substantially free of biocides" means that the gel contains less than a threshold concentration of biocides, equal to or above which the gel would cause an adverse reaction in a pest, in particular in a rodent or an insect. Preferably, the gel contains so few biocides that no biocides are detectable by conventional testing means. In preferred embodiments, "substantially free of biocides" means that the gel contains less than 0.00050 wt % biocides, preferably less than 0.00049 wt % biocides, preferably less than 0.00025 wt % biocides, preferably less than 0.00010 wt % biocides, preferably less than 0.00005 wt % biocides, preferably less than 0.00001 wt % biocides, preferably 0 wt % biocides.

By "sates the thirst of pests", this description means that a pest would consume the gel, and in doing so would provide itself with fluids, in particular water, to supplement or replace its conventional diet.

By "increases the consumption of bait", this description means that a pest would consume more bait having access to the gel than it would without such access. An exemplary test for measuring whether consumption of bait is increased is given below. However, a skilled person may readily conceive of other experiments to test whether an increase is observed without undue burden.

Figure 2:
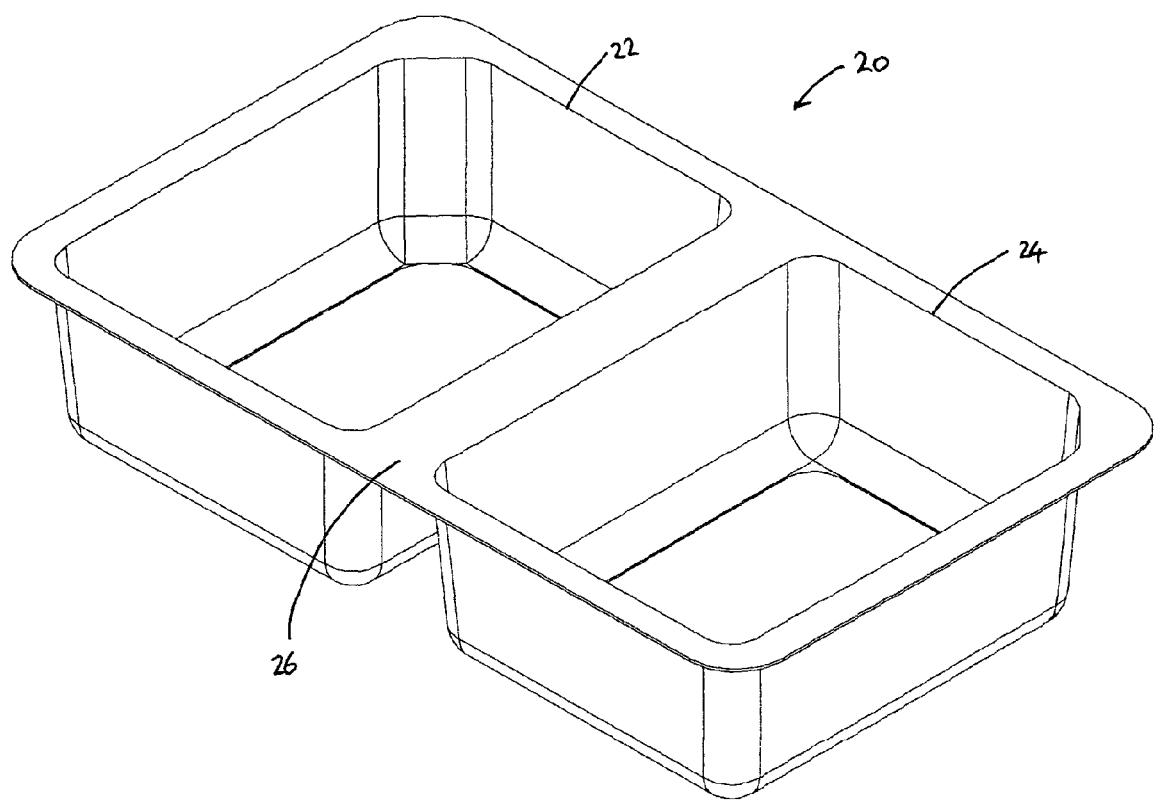

Preferred embodiments of the invention shall now be described with reference to the appended drawings, in which:

FIG. 1 is a perspective view of a first exemplary container having first and second compartments for containing a consumable gel and a poisonous material, respectively; and FIG. 2 is a perspective view of a second exemplary container having first and second compartments for containing a consumable gel and a poisonous material, respectively.

For expediency, embodiments of the invention shall hereafter be described in the context of rodent control, wherein a gel, combination, device, method and use according to the invention are used with a rodenticide, but the skilled person will understand that pest control devices according to the present invention may be used with other poisonous substances and deployed against other pests.

For example, the invention may be used with an insecticidal formulation. Such formulations are known and may comprise granular, gel, solid, or tablet type insecticides or sticky traps which comprise organophosphates, synthetic pyrethroids, insecticides acting on the nervous system, organic active ingredients, insect growth regulators, chitin inhibitors and so on.

Aspects of the invention have use in the control of rodents belonging to the family of Muridae, including the species *Rattus norvegicus, Rattus rattus, Bandicota benaglensis, Mus musculus*, and *Apedemus sylvaticus*. However, the invention may be deployed against other rodents if preferred.

Aspect of the invention also have use in the control of insects belonging to the family of Blattidae, including the species *Blatella germanica, Blatta orientalis, Periplaneta americana, Periplaneta fuliginosa/japonica*, and *Supella longipalpa*. However, the invention may be deployed against other insects if preferred.

In accordance with a first aspect, the present invention provides a consumable aqueous gel for use in pest control which sates the thirst of pests, increases the consumption of bait by pests and which is substantially free of biocides. A person skilled in the art would be familiar with the composition of aqueous gels and readily able to form such a gel based on his or her own common general knowledge. A gel for use in pest control and comprising a poisonous active agent is taught in US 2005/0181003. A skilled person may provide a gel in accordance with the present invention by following the disclosure of that document but omitting to include the active agent.

By enabling the rodent to satisfy its thirst with a consumable gel according to the first aspect of the invention, the rodent has no incentive to leave a poisonous composition. Accordingly, the rodent consumes more of the composition, and more of the rodenticide contained in the composition. Thus, the gel of the present invention leads to an increased mortality of pests.

With the exception of biocides, aqueous gels according to the present invention may comprise a variety of constituent ingredients depending on the particular use to which the gel is put. For instance, the gel may comprise one or more of an acidity regulator, a colorant, a viscosity modifier (such as a high water absorption capacity material), a flavouring and a preservative.

It is beneficial to add a colorant to the gel because certain pests, such as flying insects, are attracted to particular colours. Conversely, colours which do not occur naturally in foodstuffs (e.g. blue) may discourage humans or other animals from consuming the product. Examples of colorants which may be used are patent blue, brilliant blue, CI direct red 254, Tartazine yellow, Azorubine and Alizarin, annato, B-carotene, carmine, carmoisine, copper-clorophyllin, curcumin, enocianin, lutein, ponceau 4R, or any other similar colorant.

The amount of viscosity modifier used in the gel will have an effect on the viscosity (i.e. flowability) of the gel. If the gel is to be placed in a container to prevent displacement of the gel, a less viscous gel may be preferred such that the gel is easier to consume. If the gel is to be placed directly on to an object or surface, a more viscous gel may be preferred such that the gel maintains its form and position. Examples of viscosity modifiers which may be used are xanthan gum, carboxymethyl cellulose, polymethacrylic acid, or sodium salts thereof, guar gum, polyacrylamide, or any other similar viscosity modifier.

Flavourings may be added to the gel to act as an attractant of the pest intended to be poisoned. Different pests are attracted to different flavourings, so the particular flavouring to be used may vary accordingly. Flavourings may also be used to act as a deterrent to humans and other animals. Examples of flavourings which may be used are sodium saccharinate, sodium chloride, sodium glutamate, chocolate flavouring, anise flavouring, and vanilla flavouring, acesulfame potassium, aspartame, ethyl maltol, glutamic acid, glycine, pineapple flavouring, potassium glutamate, sugar, vinegar, or any other similar flavouring.

The gel may also comprise appetizers which encourage rodents to satisfy their hunger. In such embodiments, the rodents not only lack the incentive to leave the composition to seek out a drink, but are also encouraged to consume more of it due to their increased appetite.

Preservatives may be added to increase the longevity of the gel. Examples of preservatives which may be used are sodium benzoate, potassium sorbate, sodium salicilate and one or more parabens, benzoic acid, calcium benzoate, calcium propionate, ethyl parahydroxybenzoate, potassium benzoate, potassium propionate, propionic acid, propyl parahydroxybenzoate, sodium propionate, or any other similar preservative.

Examples of acidity regulators which may be used are lactic acid, citric acid, at least one sodium phosphate or pyrophosphate, at least one calcium phosphate or pyrophosphate, at least one potassium phosphate or pyrophosphate, at least one inorganic carbonate, or any other similar acidity regulator.

In preferred embodiments of the invention, gels comprise components in accordance with the following table.

|  | For example |  | Preferably |  |
| --- | --- | --- | --- | --- |
| Acidity regulators | Lactic acid, citric acid, sodium-calcium-or potassium phosphates, or pyrophosphates, various inorganic carbonates, or their combinations | 0.1-3.0% | Calcium lactate:<br>Citric acid: | 1.170%<br>0.100% |
| Colourant | Brillant blue, CI direct red 254, Tartazine yellow, Azorubine, Alizarin | 0.001-0.100% | Patent blue: | 0.004% |
| High water absorption capacity material | Guar gum, xantan gum, carboxy methyl cellulose (CMC), polymethacrylic acid and their sodium salts, polyacrylamides, or their combinations | 0.1-10.0% | Polyacrilamide (Optifloc MWP): | 3.680% |
| Flavoring: | Sodium saccharinate, sodium chloride, sodium glutamate, chocolate-anise-or vanilla flavoring, or their combinations | 0.05-0.25% | — | 0.000% |

-continued

|  | For example |  | Preferably |  |
|---|---|---|---|---|
| Preservative | Sodium benzoate, potassium sorbate, sodium salicilate, various kind of PARABENs or their combinations | 0.01-1.0% | Methyl parahydroxybenzoate: | 0.100% |
| Water: | — | add to 100% | Water: | 94.946% |
|  |  |  |  | 100.000% |

Whilst other compositions are also possible, as will occur to the skilled person, specific, non-limiting, examples of the gel composition are as follows:

EXAMPLE I

| Calcium-lactatet: | 1.170% |
|---|---|
| Citric acid: | 0.100% |
| Colourant: | 0.001-0.1% |
| Polyacrilamide: | 3.680% |
| Methyl parahydroxybenzoate: | 0.100% |
| Water: | Add to 100% |

EXAMPLE II

| Calcium carbonate: | 1.830% |
|---|---|
| Lactic acid: | 1.000% |
| Colourant: | 0.001-0.1% |
| Xantan gum: | 0.820% |
| Sodium saccharinate: | 0.047% |
| Vanilla flavouring: | 0.050% |
| Sodium benzoate: | 0.500% |
| Water: | Add to 100% |

EXAMPLE III

| Calcium phosphate: | 1.760% |
|---|---|
| Phosphoric acid: | 0.100% |
| Colourant: | 0.001-0.1% |
| CMC: | 1.460% |
| Sodium chloride: | 0.081% |
| Anise flavouring: | 0.020% |
| Potassium sorbate: | 0.500% |
| Water: | Add to 100% |

EXAMPLE IV

| Calcium carbonate: | 1.550% |
|---|---|
| Citric acid: | 0.960% |
| Colourant: | 0.001-0.1% |
| Guar gum: | 3.760% |
| Sodium glutamate: | 0.081% |
| Chocolate flavouring: | 0.020% |
| Propyl parahydroxybenzoate: | 0.500% |
| Water: | Add to 100% |

In accordance with a second aspect, the present invention provides a combination (or kit) for use in pest control, the combination comprising an aqueous gel which is substantially free of biocides. Preferably, the aqueous gel is in accordance with that described in respect of the first aspect of the invention, above. The gelatinous nature of an aqueous gel means that it is exceptionally versatile and can be applied to a variety of forms of bait. The bait, preferably containing a biocide such as a rodenticide or insecticide material but alternatively or additionally including other poisonous material, may be provided in the form of a composition comprising one or more of a solid material, a semi-solid material, a gel material or a liquid material.

Examples of solid materials which may form the bait composition are grain, granulate, pellet, loose bait, chippings, block or tablet, and dust. An example of a semi-solid material which may form the bait composition is a flour mixture having a high oil and/or fat content which results in a paste. As a skilled person will understand, a wide variety of solid, semi-solid, gel and liquid materials may be used to make up a bait composition.

A wide variety of biocides may be contained in the bait. For instance, in one preferred embodiment, the invention may be used with a non-toxic rodenticide formulation known to the skilled person as corn cob powder (EC No. 310-127-6, CAS 999999-99-4). This formulation causes the stomach of a rodent to bloat.

In other embodiments, the biocide may be toxic rodenticides, including: acute (such as zinc phosphide, aluminium phosphate, scilliroside, alphachloralose or thallium sulphate, for example), a first generation anti-coagulant (such as Chlorofacinone, Coumatetralyl, Warfarin or Warfarin sodium, for example) or a second generation anti-coagulant (such as Bromadiolone, Brodifacoum, Difenacoum, Difethialone, or Flocoumafen, for example).

The bait may be provided as loose material, or may take the form of a shaped body. In the latter case, the extruded body preferably contains between 10 and 40 weight percent wax, and more preferably between 20 and 30 weight percent wax. The body (which may be a block, tablet or other suitable formation) may be shaped in any known manner, included extruded, compressed, and cast.

The combination of the aqueous gel and bait may be provided in a bait box, a baiting station, or other container, and this can be advantageous to prevent displacement of the gel and/or bait, or to restrict access to the bait by humans (particularly children) or other animals. However, provision of such a container is not essential, and a particular advantage of the present invention is that the gel may be applied easily to any manner of bait. For instance, where the bait is an extruded, compressed or cast body, the gel may be distributed directly on to the body so as to be as accessible as possible for the pest. Distribution of the gel is particularly straightforward if the gel is supplied in a dispenser such as a malleable tube or the like.

In accordance with a third aspect, the present invention provides a pest control device comprising a container having a compartment containing an aqueous gel which is substantially free of biocides. Preferably, the aqueous gel is in accordance with that described in respect of the first aspect of the invention, above. Embodiments according to the third aspect of the invention are shown in FIGS. 1 and 2, described in more detail below.

The containers 10, 20 shown in FIGS. 1 and 2 comprise a first compartment 12, 22 for containing an aqueous gel and a second compartment 14, 24 for containing a bait, preferably including a rodenticide material. Naturally, the invention is not limited to the number or arrangement of compartments shown in the figures. In particular, the second compartment is optional—a container according to the invention may comprise only a first compartment 12, 22 containing an aqueous gel, which container may be placed next to a container containing a bait to encourage a rodent to consume said bait, and any rodenticide material contained therein.

Embodiments wherein the container has only a first compartment 12, 22 holding the aqueous gel may be deployed independently from the rodenticide. These embodiments are particularly suited for use in conjunction with rodent feeding crates or boxes with pre-deployed baits, for example. These embodiments may also be deployed on trays, and the like, holding baits.

The first compartment 12, 22 may be equipped with a first cover (not shown) which would be provided on top of the first compartment, thus closing it. The cover may be a steam and liquid tight cover. The cover may be made of aluminium foil, thermoplastic material, or other suitable cover material. If the cover is a thermoplastic material, it is preferably a weldable thermoplastic material such as BOPP/PVC. The cover may be affixed to compartment using adhesive which adheres to both the thermoplastic compartment and to either the aluminium foil or thermoplastic material.

Due to the vapour and liquid tight nature of the cover, the first compartment 12, 22 of the container stores the aqueous gel in the compartment until deployment without leaking. However, the cover may be easily removed upon deployment by tearing.

The second compartment 14, 24 may be equipped with an aroma and/or air permeable cover (not shown) which may be made from cellulose based material. Preferably, the cover is adapted such that it filters any allergen dust or poisonous material and prevents it from being released. Accordingly, only the aroma of the bait escapes from the second compartment. As a result, the container can be transported safely.

The first compartment 12, 22 for containing the aqueous gel and the second compartment 14, 24 for containing the bait may be connected with a connecting bridge 16, 26.

In a particularly preferred embodiment of the invention, a container with two separate compartments is provided. The container is made of a thermoplastic material such as PVC or PET, and is manufactured by vacuum shaping, pressing or molding. The container is manufactured such that a first compartment is suitable for holding an aqueous gel, and a second compartment is suitable for containing a rodenticide material, although any poisonous material may be used instead.

Of course it is possible to provide a containing having any number of compartments, each of which may be manufactured by vacuum shaping, pressing or molding, as described above. The material used to form the second compartment may be the same or a different material than that used to form the first compartment.

When a pest control device according to the invention is deployed, the first cover (if present) of the first container containing the aqueous gel is removed. The air-permeable cover (if present) of the second compartment holding the bait is not removed. Accordingly, the container according to the invention is ready for deployment.

In a fourth aspect, the present invention provides a method of controlling pests comprising the step of deploying an aqueous gel according to the aforementioned first aspect, a combination according to the aforementioned second aspect, or a pest control device according to the aforementioned third aspect. Deployment of the gel, combination or device may be carried out anywhere, but is preferably carried in a location known to be infested by a pest.

Trials Involving a Consumable Aqueous Gel

Trials were conducted to establish whether pest control devices including a gel according to aspects of the present invention provided an improvement over a standard test composition. The standard test composition (henceforth "EPA Standard") was a food mixture with no active ingredient (i.e. a placebo) consisting of: 65% corn grits, 25% oat flakes, 5% granulated sugar and 5% corn germ oil. The trials complied with the current valid guidelines, and acclimatization and pre-feeding periods were adhered to.

In one trial, 10-10 mature, healthy male and female *Rattus norvegicus* rats were selected. The rats were placed in two interconnected semi-field trail chambers, each of which was fully tiled and which had heights of 2.28 m and floor sizes of 3.1 m×1.18 m and 3.1 m×1.3 m, respectively. The total floor area was 7.69 m$^2$. Throughout the trial, the temperature was between 20 and 25° C., the relative humidity was between 45 and 50% saturation and the rats were exposed to 12 hours of light and 12 hours of darkness per day. Water was given ad libitum throughout the trial.

Four black baiting stations were placed in the chambers, together with metal tubes filled with shredded paper which served as hidden places for the rats. Two baiting stations were filled with a control diet—either the EPA Standard, or the rodenticide composition without the aqueous gel. Two other baiting stations contained the rodenticide composition together with an aqueous gel.

Every 24 hours, consumption of the composition at each baiting station was measured and refilled. In each case, mortality was 100%. The following results were obtained:

1. Results Versus EPA Standard

|  | Versus EPA standard-% | |
| --- | --- | --- |
|  | Without aqueous gel | With aqueous gel |
| Grain bait | 23.6 | 35.2 |
| Granule bait | 30.0 | 45.9 |
| Average consumption % | 26.80 | 40.55 |
| Increase of consumption % | 51.30 | |

2. Results of Product Versus Product+Aqueous Gel

|  | Product without aqueous gel % | Product with aqueous gel % |
| --- | --- | --- |
| Grain bait | 38.3 | 61.7 |
| Granule bait | 35.1 | 64.9 |
| Mix of loose and granule baits | 32.3 | 67.7 |

|  | Product without aqueous gel % | Product with aqueous gel % |
| --- | --- | --- |
| Average consumption | 35.2 | 64.8 |
| Increase consumption |  | 84.1 |

The trials clearly show that adding an aqueous gel increases the consumption of the composition. In particular, when consumption of the product is evaluated versus the same product but with an aqueous gel added, a dramatic increase of consumption—almost by double—was recorded.

It will be appreciated that modifications may be made to the embodiments described above without departing from the scope of the invention as defined by the claims.

The invention claimed is:

1. A kit for use in a pest control device, the kit comprising:
an aqueous gel, wherein the aqueous gel contains less than 0.00050 wt % biocides; and
a bait which comprises a biocide comprising a rodenticide material and/or an insecticide material.

2. A pest control device comprising:
a container having a first compartment and at least one other compartment, wherein the first compartment contains an aqueous gel, wherein the aqueous gel contains less than 0.00050 wt % biocides, and wherein the at least one other compartment contains a bait which comprises a biocide containing a rodenticide material and/or an insecticide material.

3. The pest control device according to claim 2, wherein the first compartment is equipped with a first cover adapted to close the first compartment, and one or more of the at least one other compartment is equipped with a further cover adapted to close the one or more at least one other compartment.

4. The pest control device according to claim 3, wherein each of the first and the at least one other compartments are connected to an adjacent compartment with a connecting bridge.

5. The pest control device according to claim 3, wherein the further cover is air-permeable, and is made from an aroma-permeable baize, fabric, foil or paper.

6. The pest control device according to claim 5, wherein the bait includes a composition comprising one or more of a solid material, optionally grain, granulate, pellet, loose bait, chippings, block or tablet, and/or dust, a semi-solid material, optionally a flour mixture having a high oil and/or fat content, a gel material, and/or a liquid material.

7. The pest control device according to claim 5, wherein the bait includes a composition comprising an extruded, compressed or cast body containing between 10 wt % and 40 wt % wax.

8. The pest control device according to claim 7, wherein the aqueous gel comprises:
between 0.1 wt % and 3.0 wt % of an acidity regulator;
between 0.001 wt % and 0.5 wt % of a colorant;
between 0.1 wt % and 10 wt % of a viscosity modifier; and
between 0.01 wt % and 1.0 wt % of a preservative.

9. The pest control device according to claim 8, wherein the acidity regulator comprises one or more of: lactic acid, citric acid, at least one sodium phosphate or pyrophosphate, at least one calcium phosphate or pyrophosphate, at least one potassium phosphate or pyrophosphate, or at least one inorganic carbonate.

10. The pest control device according to claim 9, wherein the acidity regulator consists of calcium lactate and citric acid.

11. The pest control device according to claim 10, wherein the colorant comprises one or more of: patent blue, brilliant blue, CI direct red 254, Tartazine yellow, Azorubine and Alizarin, annato, B-carotene, carmine, carmoisine, copper-clorophyllin, curcumin, enocianin, lutein, or ponceau 4R.

12. The pest control device according to claim 8, wherein the viscosity modifier comprises one or more of: xanthan gum, carboxymethyl cellulose, polymethacrylic acid, or sodium salts thereof, guar gum, or polyacrylamide.

13. The pest control device according to claim 12, wherein the preservative comprises one or more of: sodium benzoate, potassium sorbate, sodium salicilate and one or more parabens, benzoic acid, calcium benzoate, calcium propionate, ethyl parahydroxybenzoate, potassium benzoate, potassium propionate, propionic acid, propyl parahydroxybenzoate, or sodium propionate.

14. The pest control device according to claim 13, wherein the preservative consists of methyl parahydroxybenzoate.

15. The pest control device according to claim 14, wherein the aqueous gel further comprises between 0.01 wt % and 1.00 wt % of a flavoring.

* * * * *